US011456053B1

(12) United States Patent
Russo et al.

(10) Patent No.: US 11,456,053 B1
(45) Date of Patent: Sep. 27, 2022

(54) BIOLOGICAL MODELING FRAMEWORK

(71) Applicant: X Development LLC, Mountain View, CA (US)

(72) Inventors: Frank Russo, Sunnyvale, CA (US); Jason Donald Thompson, Redwood City, CA (US)

(73) Assignee: X Development LLC, Mountain View, CA (US)

( * ) Notice: Subject to any disclaimer, the term of this patent is extended or adjusted under 35 U.S.C. 154(b) by 1154 days.

(21) Appl. No.: 15/648,901

(22) Filed: Jul. 13, 2017

(51) Int. Cl.
*G16B 5/00* (2019.01)

(52) U.S. Cl.
CPC ..................... *G16B 5/00* (2019.02)

(58) Field of Classification Search
None
See application file for complete search history.

(56) References Cited

U.S. PATENT DOCUMENTS

| | | | |
|---|---|---|---|
| 5,966,712 A | 10/1999 | Sabatini et al. | |
| 5,970,500 A | 10/1999 | Sabatini et al. | |
| 6,023,659 A | 2/2000 | Seilhamer et al. | |
| 6,519,583 B1 | 2/2003 | Koleszar et al. | |
| 6,643,634 B2 | 11/2003 | Koleszar et al. | |
| 6,742,004 B2 | 5/2004 | Sabatini et al. | |
| 8,296,116 B2 | 10/2012 | Solomon | |
| 8,301,393 B2 | 10/2012 | Palsson et al. | |
| 2002/0091490 A1 | 7/2002 | Russo et al. | |
| 2002/0169730 A1 | 11/2002 | Lazaridis | |
| 2003/0009296 A1 | 1/2003 | Sabatini et al. | |
| 2003/0084023 A1 | 5/2003 | Koleszar et al. | |
| 2003/0124569 A1 | 7/2003 | Panzer et al. | |
| 2003/0170814 A1 | 9/2003 | Yucel et al. | |
| 2004/0014087 A1 | 1/2004 | Hodgson et al. | |
| 2004/0048253 A1 | 3/2004 | Panzer et al. | |
| 2004/0111674 A1 | 6/2004 | Koleszar et al. | |
| 2005/0095587 A1 | 5/2005 | Panzer et al. | |
| 2005/0187747 A1* | 8/2005 | Paxson | G16B 5/00 703/11 |
| 2005/0197783 A1 | 9/2005 | Kuchinsky et al. | |
| 2005/0260663 A1 | 11/2005 | Solomon | |
| 2006/0235670 A1 | 10/2006 | Vujasinovic | |
| 2007/0219768 A1 | 9/2007 | Ekins et al. | |
| 2008/0220977 A1 | 9/2008 | Imoto et al. | |
| 2010/0250218 A1 | 9/2010 | Ekins et al. | |
| 2012/0029896 A1 | 2/2012 | Ekins et al. | |
| 2017/0098032 A1 | 4/2017 | Desai et al. | |

FOREIGN PATENT DOCUMENTS

| | | | | |
|---|---|---|---|---|
| WO | WO-2008046208 A1 * | 4/2008 | ............. | G16C 10/00 |
| WO | WO2014015196 A3 | 3/2014 | | |

* cited by examiner

*Primary Examiner* — Lori A. Clow
(74) *Attorney, Agent, or Firm* — Kilpatrick Townsend & Stockton LLP

(57) ABSTRACT

Methods, systems, and apparatuses, including computer programs encoded on a computer storage medium, can be implemented to perform certain actions. The actions can include maintaining biological data related to multiple biological systems in a first format in a data repository, receiving a first selection of a biological system of the multiple biological systems for constructing a model that simulates a behavior of the biological system, retrieving a subset of data of the biological data that is associated with the first selection of the biological system, receiving a second selection of a modeling technique of the multiple modeling techniques for constructing the model, compiling the subset of biological data into configuration data of a second format that is specific to the modeling technique and that is different from the first format, and generating the model using the modeling technique and the configuration data.

20 Claims, 6 Drawing Sheets

BIOLOGICAL MODELING FRAMEWORK

BACKGROUND

This specification generally relates to a computer-implemented framework for configuring a model that simulates a behavior of a biological system.

Conventional biological modeling practices typically start with a choice of a modeling technique (e.g., a type of modeling methodology). Having chosen a methodology, a modeler may translate a biological system to be modeled into a technical form dictated by the chosen modeling technique. An ability to perform such translations is specific to the modeler and depends on an ability of the modeler to understand both the biological system being modeled and the modeling technique for simulating a behavior of the biological system. Moreover, as a model is developed and modified over time, modeling constructs will often accumulate artifacts (e.g., hidden variables or pseudo-reactions) whose purpose is to overcome technical barriers intrinsic to the chosen modeling technique, but whose relevance to the biological system being modeled is unclear.

SUMMARY

Implementations of the present disclosure are generally directed to a computer-implemented framework for configuring a model. For example, implementations of the present disclosure include computer-implemented methods for configuring, generating, and executing a model that simulates a behavior of a biological system. The computer-implemented methods are executed by one or more processors and include the actions of maintaining biological data related to multiple biological systems in a first format in a data repository, receiving a first selection of a biological system of the multiple biological systems for constructing a model that simulates a behavior of the biological system, retrieving a subset of data of the biological data that is associated with the first selection of the biological system, receiving a second selection of a modeling technique of the multiple modeling techniques for constructing the model, compiling the subset of biological data into configuration data of a second format that is specific to the modeling technique and that is different from the first format, and generating the model using the modeling technique and the configuration data.

These and other implementations can each optionally include one or more of the following features.

In some implementations, the first format is a structured format.

In some implementations, the second format is a structured format.

In some implementations, the multiple biological systems include one or more of organisms, portions of organism, genes, DNA, RNA, proteins, and small molecules.

In some implementations, the behavior is associated with one or more processes including biochemical reactions, molecular complexation processes, DNA replication and/or maintenance, RNA transcription, processes involving gene regulatory networks, intracellular transport, and transmembrane transport.

In some implementations, the method further includes receiving a third selection of the behavior of the biological system and receiving the subset of data of the biological data based in part on the third selection of the behavior of the biological system.

In some implementations, the multiple modeling techniques include ordinary differential equations (ODEs), systems of ODEs, partial differential equations (PDEs), systems of PDEs, Flux Balance Analyses, Monte-carlo simulations, and Boolean networks.

In some implementations, the model is a computational model.

In some implementations, the method further includes executing the model to simulate the behavior of the biological system.

In some implementations, the method further includes generating results that simulate the behavior of the biological system.

In some implementations, the method further includes storing the results of the model in the data repository.

In some implementations, the method further includes generating a graphical output corresponding to the results.

In some implementations, the method further includes sending the graphical output to a display device.

In some implementations, the graphical output includes a dynamic representation of the behavior of the biological system.

In some implementations, the graphical output includes a static representation of the behavior of the biological system.

In some implementations, the method further includes executing the model for one or more additional iterations.

In some implementations, generating the model includes automatically performing technical actions related to generating the model.

In some implementations, the method further includes receiving the biological data in the data repository.

Other implementations of the present disclosure include corresponding systems, apparatuses, and computer programs encoded on computer storage devices that are configured to perform the actions of the computer-implemented method. For example, the systems may include one or more processors and a computer-readable storage medium coupled to the one or more processors having instructions stored thereon which, when executed by the one or more processors, cause the one or more processors to perform operations in accordance with implementations of the methods provided herein.

The subject matter described in this specification can be implemented in particular embodiments so as to realize one or more of the following advantages. Computer-implemented systems disclosed herein are configured to perform methods that include configuring and generating a model that simulates a behavior of a biological system in a manner that decouples a technical skill level of a modeler from his or her scientific understanding of the biological system. For example, systems disclosed herein include a compiler that can receive (e.g., via one or more user interfaces) indications of a subject biological system, a subject behavior of the biological system, a preferred modeling technique, and additional information associated with the technique for constructing the model. The compiler can, in a robust manner, retrieve an appropriate subset of biological data (e.g., data that is particularly associated with the biological system and/or the behavior) from a much larger knowledge base of biological data stored in a data repository.

The compiler can translate (e.g., convert) the biological data from a first format to a second structured format to produce model configuration data that is suitable for the selected modeling technique. For example, the compiler can automatically perform technical steps to generate the model based on the selection of the modeling technique and the model configuration data without receiving certain additional technical parameters or inputs from the user that would otherwise be associated with generating the model. In this manner, the system can produce a model that is both robust and suitable for simulating the behavior of the biological system, irrespective of a technical ability of the user. The compiler can select technical parameters that best fit goals for modeling the behavior of the biological system while accounting for constraints of the selected modeling technique without implementation details of the model generation process altering a veracity of the biological data. Accordingly, the system avoids or minimizes generation of model artifacts (e.g., model adjustment parameters or "fudge factors") that are unrelated to the biological system and that may otherwise complicate analyses of the biological system. Therefore, the user does not need an advanced understanding of the technical implementation details of the model generation and can focus on high-level scientific aspects of the biological system.

In some examples, upon receiving indications of a selected biological system, selected biological behavior, and preferred modeling technique, the compiler can determine that the selected modeling technique is not suitable for simulating the selected behavior of the selected biological system and send a corresponding indication to an output engine for display to a user (e.g., a modeler or a system administrator) to prompt the user to select a different modeling technique. In this regard, the system may improve the user's understanding regarding certain modeling approaches and conserve resources that the user might otherwise expend to pursue an inappropriate or sub-optimal modeling approach.

In some instances, while attempting to retrieve an appropriate subset of biological data from the knowledge base, the compiler can determine that the knowledge base lacks pertinent biological data needed to model the selected behavior of the selected biological system using the selected modeling technique. Similarly, the compiler can send a corresponding indication to the output engine for display to the user, which may prompt the user to supplement the knowledge base with additional known biological data or inform the user that in silico or in vivo experiments should be performed in an attempt to determine the needed biological data. In some implementations, the compiler can execute a model and send results of the model directly to the knowledge base, thereby augmenting the knowledge base with in silico experiments.

It is appreciated that methods in accordance with the present disclosure can include any combination of the aspects and features described herein. That is, methods in accordance with the present disclosure are not limited to the combinations of aspects and features specifically described herein, but also include any combination of the aspects and features provided.

The details of one or more implementations of the present disclosure are set forth in the accompanying drawings and the description below. Other features and advantages of the present disclosure will be apparent from the description and drawings, and from the claims.

DETAILED DESCRIPTION

Figure 1:
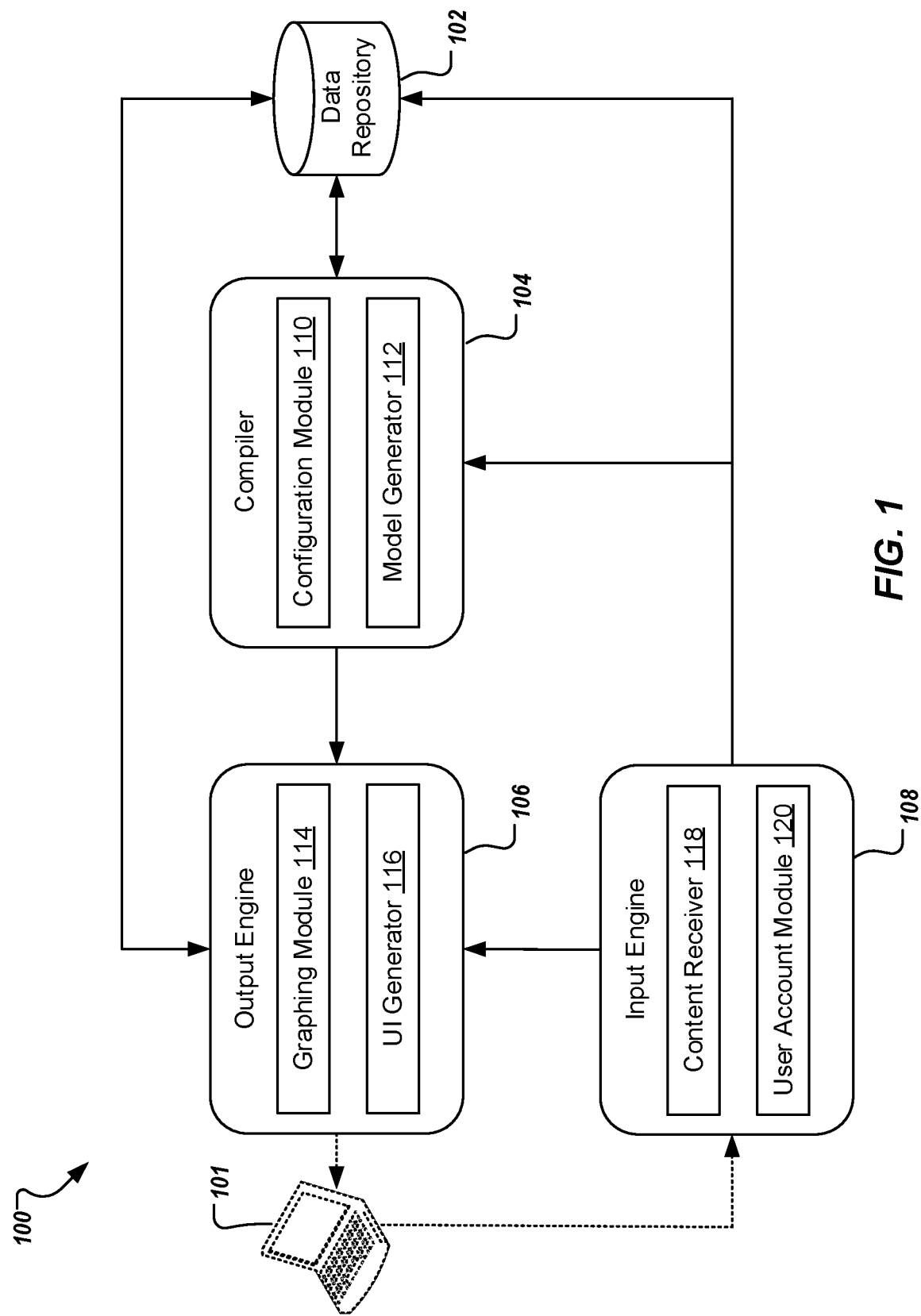
FIG. 1 depicts an example model configuration system in accordance with implementations of the present disclosure.

Implementations of the present disclosure are generally directed to a computer-implemented system that can generate a model for simulating a behavior of a biological system in a manner that decouples a technical ability of the modeler from the modeler's knowledge of the biological system. For example, the computer-implemented system includes a repository that stores biological data in a first format and a compiler that can convert the biological data into a different format that is appropriate for a particular modeling technique selected by the modeler.

In one aspect, the biological data is generally comprehendible to biological scientists and generally does not include information related to details of various modeling methodologies. In another aspect, the compiler is configured to retrieve a subset of the biological data that is associated with the subject biological system and to generate model configuration data of the second format based on the modeling technique selected by the modeler. The compiler is further configured to generate a model based on the model configuration data so that the behavior of the biological system can be simulated. The compiler performs the detailed technical aspects of generating the model such that the modeler does not need an advanced understanding of the biological system and can therefore focus on high-level aspects of generating the model. In this manner, the compiler also avoids or minimizes the generation of model artifacts (e.g., technical model adjustment parameters) that are unrelated to the biological system and that may otherwise complicate analyses of the biological system.

Implementations of the present disclosure are described herein in a non-limiting, example context that includes biological systems. More particularly, implementations of the present disclosure reference an example model configuration tool that can configure, generate, and execute a model that simulates a behavior of a biological system. It is appreciated, however, that implementations of the present disclosure are applicable in other contexts. For example, implementations of the present disclosure may also be used to simulate a behavior of other types of systems, such as chemical systems, physical systems, materials science systems, or combinations of any these systems.

Within the non-limiting example context discussed herein, implementations of the present disclosure will be described with respect to an example tool (e.g., one or more software programs executed on a server system) that can generate a model for simulating (e.g., predicting and/or illustrating) one or more behaviors of a biological system. In implementations of the present disclosure, client computing devices can present user interfaces that are generated by the tool and that are configured to receive inputs from a user (e.g., a modeler or an administrator) of the tool. The inputs are sent over a network to a server system on which the tool is executed. The server system can store the inputs, generate outputs (e.g., user interfaces including graphical and textual outputs) based on the inputs, and send the outputs over the network to one or more of the client computing devices. The one or more client computing devices can display the outputs to the user of the tool.

FIG. 1 depicts an example model configuration system 100 (e.g., a system of one or more computers that provides a biological modeling framework) in accordance with implementations of the present disclosure. The model configuration system 100 can be implemented on a mobile device or one or more server systems. The model configuration system 100 can receive a selection of a biological system and a selection of a modeling technique from a user (e.g., the model configuration system 100 can receive an indication of the biological system and an indication of the modeling technique via a user interface), retrieve a subset of data related to the biological system, and generate an appropriate model based on the subset of data and the selections to simulate a behavior of the biological system. The model configuration system 100 includes a data repository 102, a compiler 104, an output engine 106, and an input engine 108.

The data repository 102 stores a knowledge base of biological data. The biological data originates from a variety of sources and is sent to the model configuration system 100 over a network. The biological data may relate to multiple different biological systems and is generally comprehendible (e.g., from a scientific standpoint) to biological scientists. For example, the biological data may be related to one or more of: genes, ribonucleic acid (RNA) transcripts, proteins, biochemical reactions, small molecules, molecular complexation, deoxyribonucleic acid (DNA) replication and maintenance, gene regulatory networks, intracellular transport, transmembrane transport, or other biological aspects. In some examples, the biological data may not be comprehendible (e.g., from a scientific standpoint) or may only be minimally comprehendible to the user (e.g., a modeler) of the model configuration system 100. The data repository 102 can also store models, model configuration data, and graphical outputs generated by the compiler 104. The data repository 102 can additionally store user profile data associated with user accounts of the model configuration system 100.

The biological data provides core knowledge about the biological systems and is fundamentally true from a biological perspective, irrespective of a particular modeling technique. For example, the biological data may include knowledge about a particular molecule and a reaction that involves the molecule, but not technical constraints employed by a particular modeling technique used to simulate the reaction. The biological data includes information at various levels of abstraction (e.g., detail) with a fundamental premise that molecules (or other types of compounds) play roles in processes. For purposes of model generation and analysis, the biological data within the data repository 102 is assumed to be true. The biological data can be revised (e.g., changed, supplemented, or removed) by an administrator of the model configuration system 100 or by an individual who is otherwise a contributor to the data repository 102.

Figure 2:
FIG. 2 depicts a shorthand notation of an example relationship between a compound A and a protein P at a first level of detail.
Figure 3:
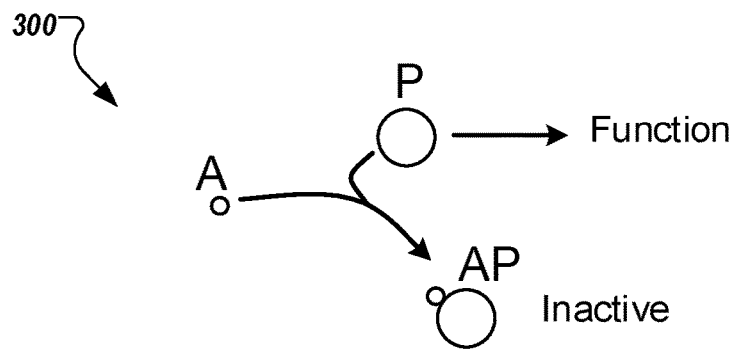
FIG. 3 depicts a shorthand notation of an example relationship between the compound A and the protein P of FIG. 1 at a second level of detail.

In an example case, at a high level, compound A may be a known inhibitor of protein P and may be represented by a shorthand notation 200 shown in FIG. 2. At a more detailed level, A may be known to reversibly bind to P, and the unbound form of P may be known to be active in some other processes, which may be represented by a shorthand notation 300 shown in FIG. 3. Both of these conditions are true and can be reflected in the biological data stored in the data repository 102, irrespective of implementation details of various modeling techniques. In some examples, there is a correlation between a type of a process and a number of roles played by molecules in the process such that as the amount of biological data grows, the number of roles played by molecules in the process can evolve.

Figure 4:
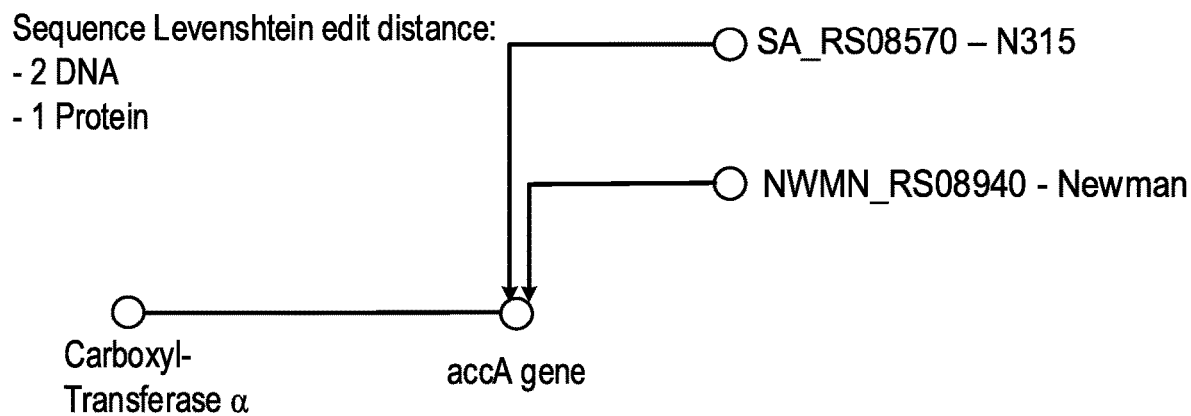
FIG. 4 depicts an example notation that describes biological data stored within a data repository of the model configuration tool of FIG. 1.

In another example, the biological data is based on pan-genes and pan-proteins as related to complex formation and roles played in processes, as illustrated in the example notation 400 of FIG. 4. Here, two strains of *S. aureus* each contain a gene, accA, encoding for the carboxyl-transferase α enzyme. The genetic sequences and the resulting protein sequences of the accA genes are not identical. However, the knowledge base captures the equivalence of the function of the two non-identical enzymes. In some examples, each strain contains a selection from available pan-genes as related to genome coordinates and strain-specific sequence variation.

The biological data may originate from publically available literature (e.g., published scientific papers or supplementary data published along with such papers) provided by various electronic sources (e.g., databases, websites, or Rich Site Summary (RSS) feeds) accessible to the model configuration system 100. For example, the biological data may be retrieved according to an automated query performed at a periodic or other predetermined schedule. In some implementations, the biological data may be entered manually by a user (e.g., an administrator) of the model configuration system 100. In some examples, the biological data is received in electronic form directly from experiments (e.g., from results produced by in silico modeling experiments). In some implementations, the data repository 102 has a storage capacity that is related to a complexity and a connectedness of the biological data and less related to an amount of the biological data, which may number in the thousands or millions of data points with respect to genes, metabolites, and reactions.

The biological data may be stored in a structured format within the data repository 102, describing both the details of a given biological object and its relationships to other objects. The biological data may stored in more than one structured format (e.g., one or more non-generic structured formats). That is, the list of attributes for a molecule is explicit and may be different from the list of attributes for a process. For example, the detailed description of a molecule may include its type (e.g., protein), an encoding gene attribute for the molecule (e.g., which may specify another type of molecule, such as DNA), its molecular weight, and a source of the data. Its relationships may include its role in one or more reactions, or its place as a subunit in a protein complex. In some examples, entries in the table may be cross-referenced with entries in other tables within the data repository 102. In some examples, the tables may include text-based indexing of molecule names for facilitating use of editing tools. In some examples, the tables may include cross-indexing of compounds, reactions, and genes for facilitating navigation of relationships.

From the input engine 108, the compiler 104 can receive an indication of a subject (e.g., particular) biological system, an indication of a behavior (e.g., a particular candidate behavior) of the biological system, and an indication of a desired modeling technique (e.g., modeling methodology) for constructing a model that simulates the behavior of the biological system. In some examples, the indications correspond to selections provided by the user at user interfaces displayed on a client computing device 101 (e.g., a data processing device). The compiler 104 can also retrieve a subset of the biological data, that, in the data repository 102, is associated with the biological system and/or the behavior to generate a model based on the subset of biological data. Accordingly, the compiler 104 includes a configuration module 110 and a model generator 112.

The configuration module 110 can receive information including the indication of the biological system, the indication of the behavior, and other information related to the biological system from the input engine 108 and can retrieve the appropriate subset of biological data from the data repository 102 based on the information. For example, the information may include one or more indications in an organism, a portion of an organism, and conditions in which the organism or the portion of the organism will be simulated.

The configuration module 110 can also receive one or more pieces of information related to the modeling technique from the input engine 108. For example, the information may include one or more indications corresponding to a particular or preferred modeling technique, a speed at which the modeling technique should be executed, a number of iterations for which the modeling technique should be executed, or a level of detail associated with the modeling technique. Example modeling techniques include ordinary differential equations (ODEs) and systems of ODEs (e.g., analytical solutions to ODEs, approximate analytical solutions of ODEs, discretized numerical solutions of ODEs, Stochastic ODEs, and other types of or solutions to ODEs), partial differential equations (PDEs) and systems of PDEs (e.g., analytical solutions to PDEs, approximate analytical solutions of PDEs, discretized numerical solutions of PDEs, Stochastic PDEs, and other types of or solutions to PDEs), Flux Balance Analyses, Monte-carlo simulations, and Boolean networks. In some implementations, the one or more pieces of information may correspond to a hybrid modeling technique that is based on more than one type of modeling technique.

In some implementations, the configuration module 110 may determine that the selected modeling technique is not suitable for simulating the selected behavior of the selected biological system and send a corresponding indication to the output engine 106 for display to the user to prompt the user to select a different modeling technique. In some implementations, the configuration module 110 may determine that the data repository 102 lacks pertinent biological data needed to model the selected behavior of the selected biological system using the selected modeling technique. The configuration module 110 may send a corresponding indication to the output engine 106 for display to the user, an administrator of the model configuration system 100, or a contributor to the data repository 102.

The configuration module 110 compiles the biological data (e.g., converts the biological data from a first structured format to a second structured format) to produce model configuration data that is suitable for the selected modeling technique. For example, the model generator 112 automatically performs technical steps to generate a model (e.g., a computational model) based on the selection of the modeling technique and the model configuration data without receiving certain additional technical parameters or inputs from the user that would be associated with generating the model, such as time step sizes, probability distributions for Monte Carlo simulations, spatial discretization for PDE models, numerical integration algorithms, parameter fitting methods, etc. In this manner, the model configuration system 100 can produce a model that is both robust and suitable for simulating the behavior of the biological system, irrespective of a technical ability of a modeler. The model generator 112 can select technical parameters that best fit goals for modeling the behavior of the biological system while accounting for constraints of the selected modeling technique without implementation details of the model generation process altering core knowledge of the biological data. Accordingly, the model generator 112 avoids or minimizes generation of model artifacts (e.g., model adjustment parameters or "fudge factors") that are unrelated to the biological system and that may otherwise complicate analyses of the biological system. Therefore, the user does not need an advanced understanding of technical implementation details of the model generation and can focus on high-level scientific aspects of the biological system. Example technical steps that may be agnostic to the type of modeling methodology selected and that may be performed by the model generator 112 to generate the model include choosing time step sizes, choosing probability distributions, performing parameter fitting, performing spatial discretization, performing numerical integrator tuning, and paring down the total number of available modeling methods based on the quality and resolution of the data in the knowledge base. In some implementations, such technical steps are agnostic Once the model is generated, the model generator 112 can execute (e.g., run) the model to produce results that simulate the behavior of the biological system and send the results to the output engine 106 for display of the results to the user. The model generator 112 may execute the model automatically after generating the model or execute the model on-demand in response to a request from the input engine 108 (e.g., provided by the user at a user interface). In some examples, the model generator 112 may execute the model for a particular number of iterations that is specified by the user at a user interface or execute the model for a number of iterations that is automatically determined by the model generator 112 based on the selected modeling technique. In some implementations, a user may be interested in modeling a particular biological process, rather than specifying a number of iterations. For example, the user may want to know what happens to a particular protein over 10 cell cycles. The model generator 112 will determine an appropriate time step size given some desired level of precision and then determine the number of iterations as the multiplication of the time step, a duration of the time step, and the number of time steps (10, in this example). The model generator 112 can also send either or both of the model and the results to the data repository 102 for storage and future retrieval.

The output engine 106 includes a graphing module 114 and a user interface (UI) generator 116. The output engine 106 can receive model results from the compiler 104, stored model results from the data repository 102, instructions from the input engine 108, and user profile information from the data repository 102. The graphing module 114 can plot computational model results in a variety of coordinate systems to generate multiple types of graphical outputs, as well as tables (e.g., matrices). In some examples, the model results may be provided as non-computational and/or qualitative results, depending on the selected modeling technique and associated post-processing. For example, a user may want to know if a set of conditions will induce a virulent phenotype of the organism of interest. In such a scenario, the output may be that the set of conditions induces virulence or that the set of conditions does not induce virulence. In some examples, the graphical outputs are static representations of the biological system, such as bar graphs, line graphs, charts, or maps. In some examples, the graphical outputs are dynamic representations of the biological system, such as animations. In some examples, the output engine 106 sends the graphical outputs to the data repository 102 for storage. In some examples, the graphing module 114 sends the graphical outputs to the UI generator 116 for integration into various user interfaces that can be outputted to one or more computing devices, such as the client computing device 101. That is, the output engine 106 can provide the graphical outputs for presentation in a user interface being presented on a display of a processing device (e.g., for presentation in a web browser or a special-purpose application executing on the processing device and configured to interact with the model configuration system 100 over a network). In some examples, the output engine 106 provides a subset of the generated graphical outputs to the processing device based on a user selection of desired graphical outputs. In some examples, the output engine 106 provides all of the generated graphical outputs to the processing device.

The UI generator 116 can generate various user interfaces that are provided to the output engine 106. In some embodiments, the user interfaces may be command line interfaces. The user interfaces may include biological data interfaces by which contributors (e.g., biological scientists, and modelers) to the data repository 102 can input biological data or configure storage parameters of the biological data, model configuration interfaces (e.g., via scripting and direct modification of code in some examples) by which modelers can input a selection of a biological system, a selection of a behavior of the biological system, a selection of conditions in which the biological system will be simulated (e.g., a temperature and nutrients in media or other parameters related to a chemical environment), a selection of a modeling technique and associated parameters, a selection of a graphical output format for model results, and user account interfaces by which modelers and contributors can access respective functionalities of the model configuration system 100. The various user interfaces can include pull-down lists, toggle switches, blank input fields, formatted text documents (e.g., for large numbers of parameters), and slider bars by which users can input information to the model configuration system 100.

In some examples, the biological data interfaces can provide mechanisms for adding, editing, and validating individual entries for compounds, reactions, genes, proteins, complexes, and relationships among any of these entities. In some implementations, the biological data interfaces serve as part of rigorous tooling that can enable deep curation by a large number of contributors and in a manner that preserves a basic correctness of the biological data from a scientific perspective. In some implementations, such tooling may include natural language processing capabilities to allow automated extraction of biological data from scientific literature.

The input engine 108 includes a content receiver 118 and a user account module 120. The content receiver 118 can receive substantive inputs provided in the biological data and model configuration interfaces, and the user account module 120 can receive user profile data (e.g., a user login and password and other user profile data) provided in the user account interfaces. In some examples, the content receiver 118 sends the substantive inputs to the data repository 102 for storage in association with a subset of the biological data, a stored model, or a user account. In some examples, the content receiver 118 generates and sends an instruction to the output engine 106 to generate and output a subsequent user interface based on a substantive input. For example, the instruction, when executed, can cause one or more server systems on which the output engine 106 is implemented to generate and output a subsequent user interface.

In some examples, the user account module 120 accesses user profile data stored in the data repository 102 to verify the user profile data entered into the user account interfaces. According to a result of the verification (e.g., valid account access information or invalid account access information), the input engine 108 generates and sends an instruction to the output engine 106 to generate and output a subsequent user interface (e.g., a biological data interface or a model configuration interface). For example, the instruction, when executed, can cause one or more server systems on which the output engine 106 is implemented to generate and output a subsequent user interface.

Figure 5:
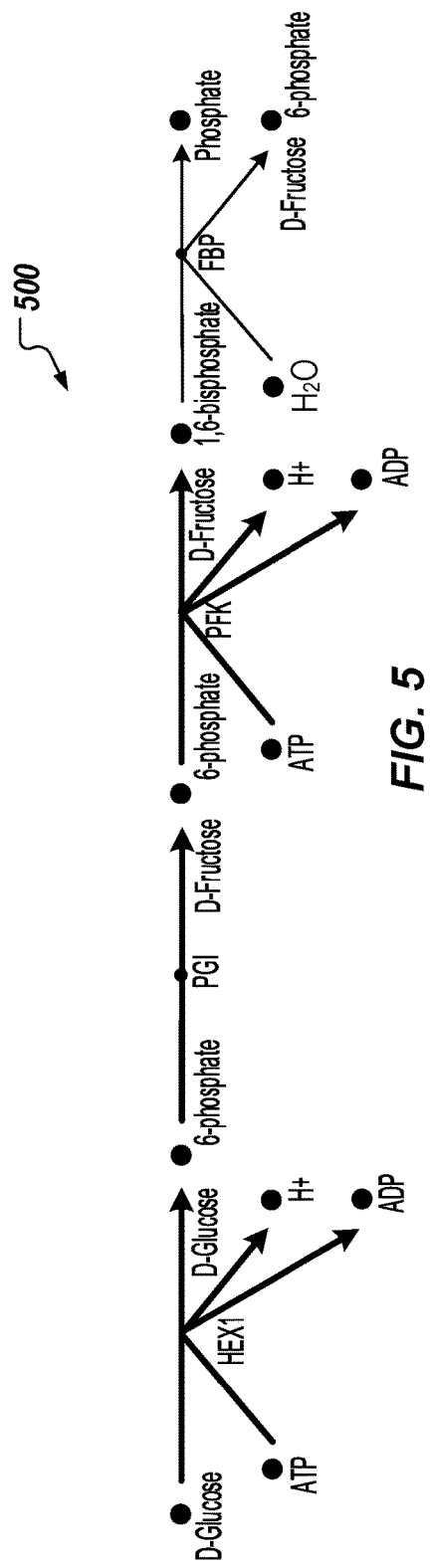
FIG. 5 depicts an example visualization related to model results produced by a model generated by the model configuration tool of FIG. 1.

In some implementations, once one or more models are generated and executed to produce results, those results can be analyzed to further inform or augment the biological data in the data repository 102. For example, parameters associated with the generated models can be changed, different types of models can be compared to one another, and/or additional model iterations can be executed to investigate how the models behave over a range of conditions or how simulation results change as model construction changes. Such investigations may clarify which parts of the model are most essential under different biological growth conditions and how some portions of the model compensate if different portions of the model are disabled. In one example, FIG. 5 displays an example visualization 500 that is useful in showing flux across reactions in a chain. The visualization 500 represents a part of a metabolic process that converts glucose into fructose 6-phosphate and phosphate. The blue dots represent chemical species produced and consumed in reactions, and the lines represent reaction directions, with the weight of the lines representing a flux of material flowing through each reaction. Under different simulated conditions or with different modeling methodologies, the overall structure of the visualization 500 will remain the same, as it is defined by data in the knowledge base. However, weights of the various lines may differ for different simulated conditions or with different modeling methodologies.

Furthermore, empirical data (e.g., experimental data) may be used to fine-tune aspects of model generation carried out by the model generation system 100 by exposing a need for additional constraints and providing new relationships that can be incorporated into a model. In some examples, wet-lab type approaches may be used to explore model predictions and fill in gaps of model predictions. In an example of a model-driven experiment and as related to growth profiles, metabolic models can make predictions of relative uptake of various components, excretion of waste products, and relative growth rates in different media for a given biological medium composition. All of these aspects can be examined experimentally, with any discrepancies between experiments and models suggesting that parts of the models may need to be adjusted. In some implementations, a suite of tools may be used to analyze differences between models and experiments and may depend on the specific experiments being performed and the specific biological question being asked.

In another specific example of a model-driven experiment and as related to gene characterization, a majority of gene function assignments in *S. aureus* are based on homology to better-characterized systems, such as *B. subtilis* or *E. coli*. In many such cases, there may be two or more homologs assigned to a given function. Knockouts or other experimental techniques may clarify these cases. Transport functions may be particularly useful tools in such examples. Knockouts of individual transporters may be very targeted in terms of what they can or cannot use from an external medium.

In some examples, simulated behavior of the biological system may be used as a tool that facilitates interpretation of experimental results. For example, the model generation system 100 can run multiple in silico experiments (e.g., execute multiple model iterations) in order to perform fewer wet-lab experiments. Furthermore, gaps in in-silico understanding can guide priorities of wet-lab experiments. In some examples, in silico experiments can be used to interpret RNA expression results in context. In an example of experiment-driven modeling and as related to RNA sequencing, large-scale transcription studies will be a rich source of hard data to use in modeling. A wide variety of growth conditions can be examined to explore which genes, and therefore which reactions or other processes, are active. Analyzing this data in the context of effects on the model can provide more insight on parts that are understood and highlight the areas that are not well understood. Such clarification can be particularly powerful in providing clues to the functions of genes not yet assigned in modeling terms.

In another example of experiment-driven modeling and as related to metabolomics, a large part of modeling methodology deals with compensating for a lack of hard data for large parts of a biological system. FBA may not require a lot of detail regarding kinetic parameters of any of enzymes, reactions, or concentrations of metabolites. However, if such data is available, the data may be used to constrain behavior of models in much more detail.

In an example of generating a model (e.g., a computational model) using the model configuration system 100, metabolic behavior of a biological system can be modeled using FBA, which transforms the metabolic network into a linear programming problem. A FluxBalanceAnalysis class can be defined to facilitate translation of concepts and structures related to the biological data into constructs that are specific to FBA. An example use-case can be illustrated with example python code:

[1] fba=FluxBalanceAnalysis( )
[2] for rxn in reactions.values( ):
[3] fba.add_reaction(rxn)
[4] for exch in exchanges.values( ):
[5] fba.add_exchange_flux(exch, [−5, 5])
[6] for component, value in
   biomass.items( ):
     fba.add_objective (compounds[component], −value)
[7] fba.add_objective (compounds[component], −value)
[8] fba.build( )
[9] fba.solve( )

By changing the list of included reactions, components of the biomass, etc., variants of the model can be quickly iterated. In some implementations, such iterations can be performed using python code. In some examples, a set of named model configurations can be used, which may allow results of a given execution to be tied to a known configuration and allow new model configurations to be defined as modifications of existing ones. For example, a canonical *S. aureus* Newman model can be defined, and then multiple in silico experiments can be executed, each with a minor modification to this model. In this example, all inputs above the fba.build( ) command are input by the user. For example, the user is instructing the compiler 104 to use FBA as the modeling methodology (line 1), which reactions to include (lines 2 and 3), which exchange fluxes to include (lines 4 and 5), and what the objective function is (lines 6 and 7). the fba.build( )command (line 8) is invoking the compiler 104. The compiler 104 will turn the above set of parameters into a mathematical representation that can be solved through linear optimization. Accordingly, the user is specifying biological concepts, including reactions, flux constraints, and a biomass specification. However, the compiler 104 chooses a linear optimizer, generates mathematical constraints from reaction stoichiometry and flux constraints, and generates an objective function from the biomass specification. The constraints and the objective function are then input to the linear optimizer, and a solution returned with fba.solve( ) (line 9).

In some examples, the compiler 104 is configured such that the user is requested to specify even fewer methodology-specific parameters (e.g., 'exchange flux' and 'objective function' of lines 4-5 above) so that the user can think only in biological terms (e.g., 'medium composition'). In such implementations, a framework code of the compiler 104 can translate the biological terms into methodology-specific terms (e.g., 'exchange flux') and translate the methodology-specific results back into biological terms (e.g., referring to line 9 above, a solved value of an exchange flux may be expressed as an uptake rate of a compound from a medium).

In another example of generating a model using the model configuration system 100, a model configuration can be built directly from a genome sequence. At a first level, this involves finding which genes are present or absent in a particular biological organism and including only the reactions or other processes enabled by such genes. At a next level, this involves understanding impacts of known variants, such as by adjusting kinetics of a transport step based on which allele of an encoding gene is present.

Figure 6:
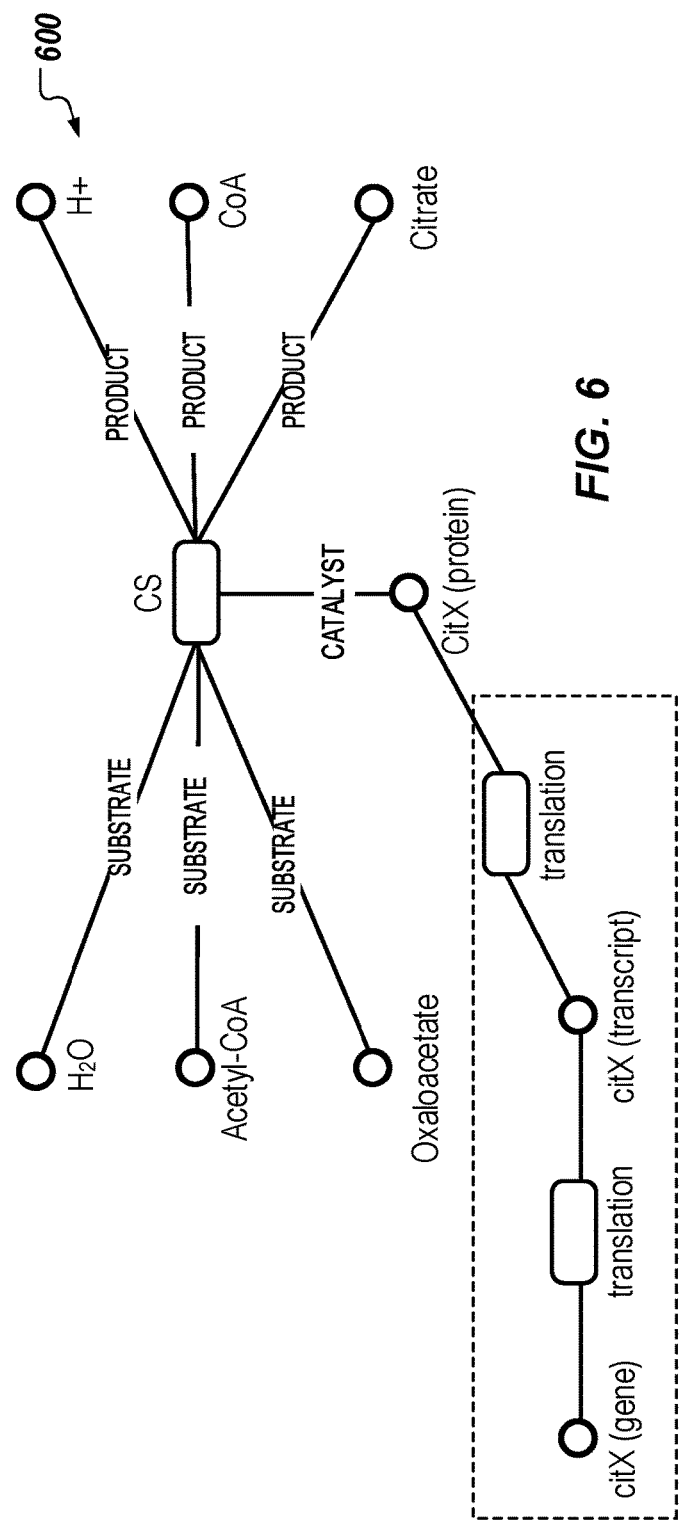
FIG. 6 depicts an example subset of knowledge stored within the data repository of the model configuration tool of FIG. 1.

In an example of biological data storage within the data repository 102, a citrate synthase reaction can be represented according to a knowledge subset 600 depicted in FIG. 6. The knowledge subset 600 is a labeled bipartite graph, with edges between molecule and process (e.g., reaction) nodes. Proteins (e.g., citrate synthase) are encoded by genes and may need to go through additional processes (e.g., such as maturation and complexation) to produce a molecular entity that is an actual participant in a reaction. The example of FIG. 6 uses a metabolic reaction to illustrate relationships, however, in other implementations, the same fundamental model can cover other types of processes as well, such as regulation, complex formation, and gene expression.

In another example of biological data storage within the data repository 102, a unified model of the *S. aureus* pan-genome can be built with genes from individual strains such as *S. aureus* N315 or *S. aureus* Newman mapped to corresponding pan-genes. Such a mapping may include an edit distance for how far the strain-specific version of a gene differs from a reference pan-gene. For citrate synthase, there are three nucleotide differences between N315 and Newman, and none of these differences occur at the protein level. In some examples, core knowledge about each pan-gene may be universal, regardless of where the pan-gene appears.

Figure 7:
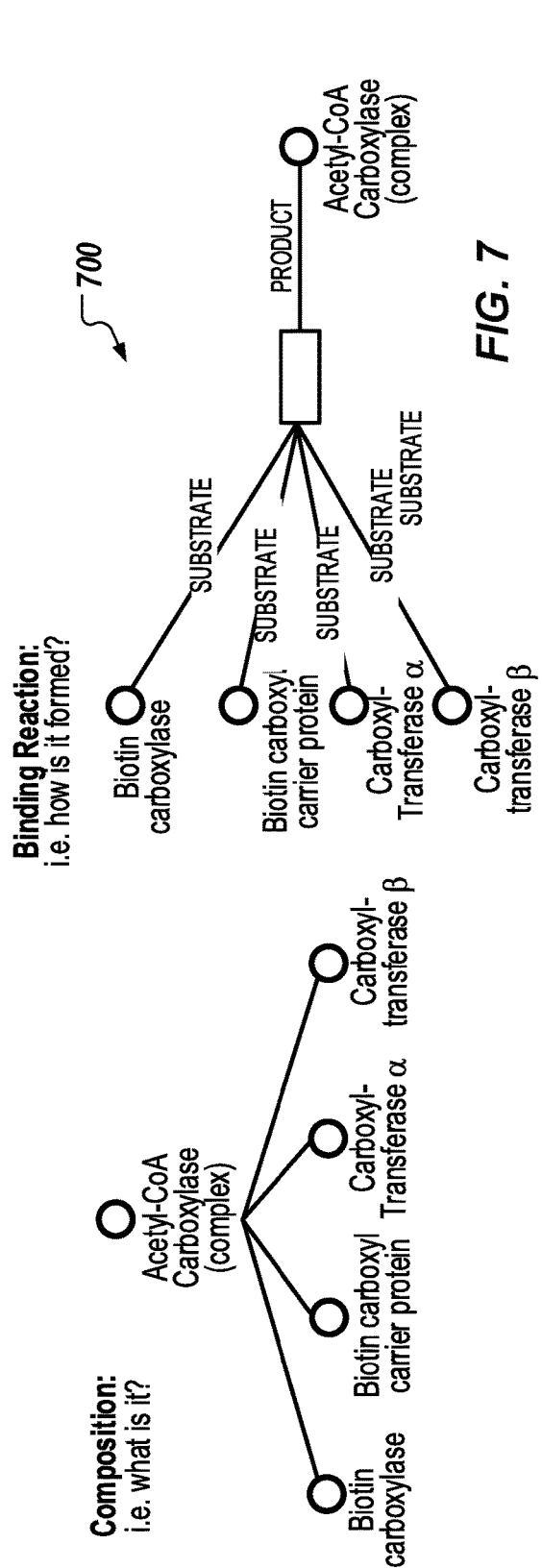
FIG. 7 depicts an example composition and binding reaction that may be modeled using the model configuration tool of FIG. 1.

In another example of biological data storage within the data repository 102, a composition and binding reaction 700 shown in FIG. 7 may be modeled using the model configuration system 100. Biotin Carboxylase, for instance, may be described as an independent protein with a molecular weight and an isoelectric point. It is also one subunit of the complex named Acetyl-CoA Carboxylase, stored in the data repository as a separate molecule with its own molecular weight and isoelectric point. These two molecules have a structural relationship (subunit to complex) and play distinct roles in a binding reaction (substrate and product).

Figure 8:
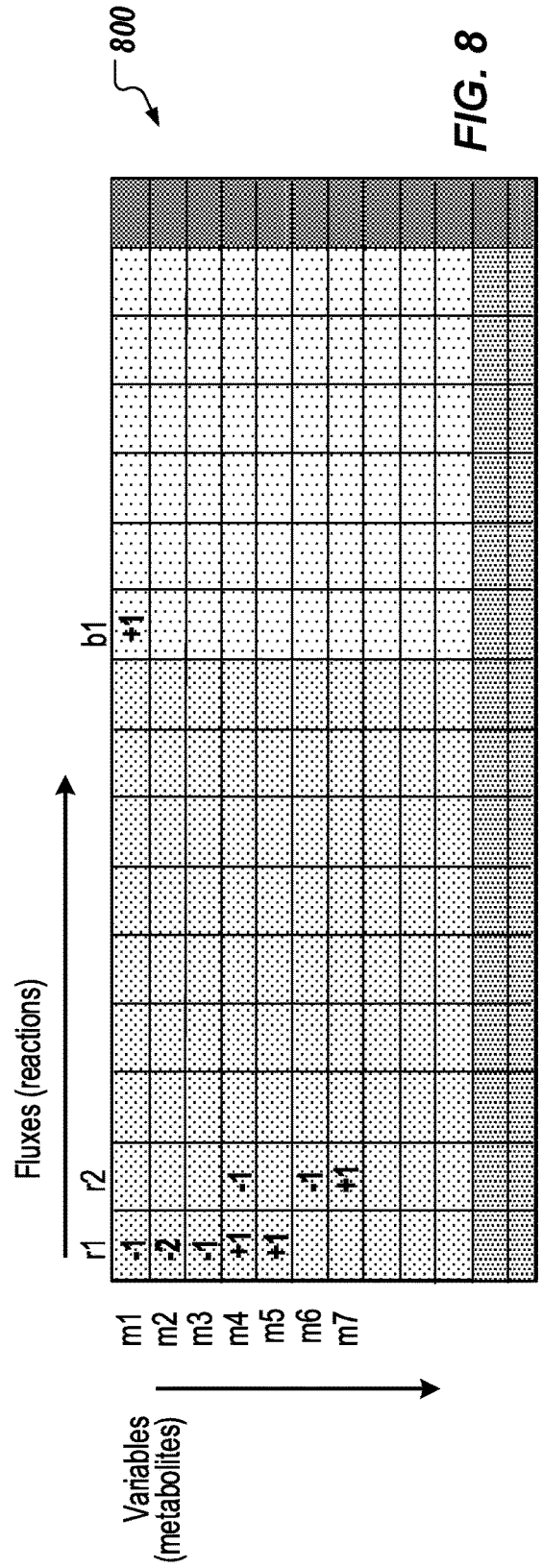
FIG. 8 depicts a flux balance analysis generated by the model configuration tool of FIG. 2.

In another example of generating a model using the model configuration system 100 (e.g., a methodology-specific structure produced by the compiler 104), a Stoichiometry Matrix 800 shown in FIG. 8 may be generated using the model configuration system 100. For example, the FBA 800 is an example of how the constraints and fluxes of the above-discussed example python code use-case are represented mathematically. This is a structure specific to the FBA methodology, and would not be easily comprehendible to a typical user who does understand the biological system. The compiler 104 translates specifications of reactions, medium composition, and other factors into this form, which defines the constraints for a linear-programming problem.

Figure 9:
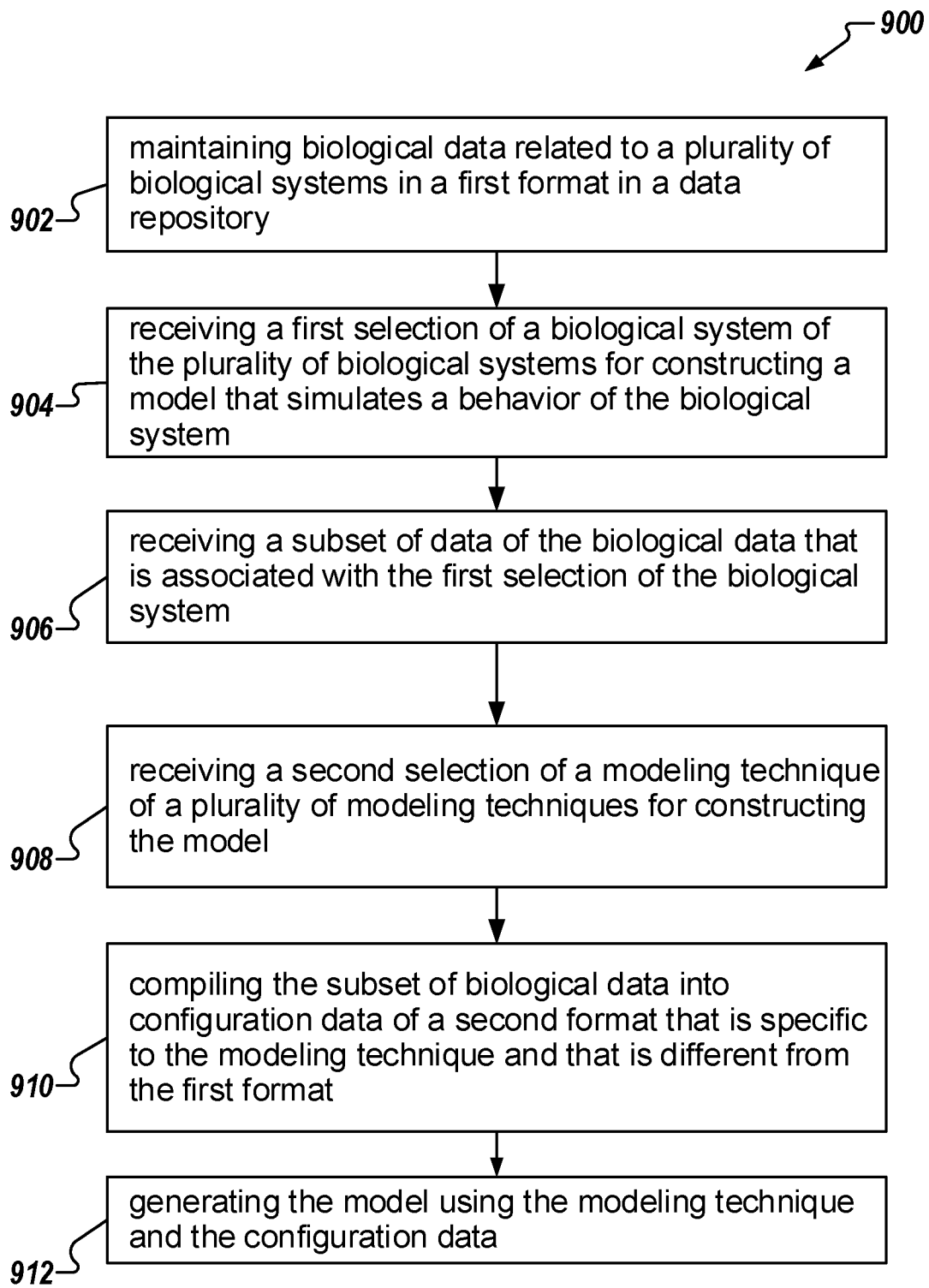
FIG. 9 depicts an example process that can be executed in implementations of the present disclosure.

FIG. 9 depicts an example process 900 that can be performed in implementations of the present disclosure. The example process 900 can be performed, for example, by the model configuration system 900 of FIG. 1. In some implementations, the process 900 includes maintaining biological data related to multiple biological systems in a first format in a data repository (e.g., the data repository 102) (902). In some examples, the process 900 further includes receiving the biological data in the data repository. In some examples, the first format is a structured format. In some implementations, the process 900 further includes receiving a first selection of a biological system of the multiple biological systems for constructing a model that simulates a behavior of the biological system (904). In some examples, the model is a computational model. In some examples, the biological systems include one or more of organisms, portions of organism, genes, DNA, RNA, proteins, and small molecules. In some examples, the behavior is associated with one or more processes including biochemical reactions, molecular complexation processes, DNA replication and/or maintenance, RNA transcription, processes involving gene regulatory networks, intracellular transport, and transmembrane transport.

In some implementations, the process 900 includes retrieving a subset of data of the biological data that is associated with the first selection of the biological system (906) and receiving a second selection of a modeling technique of multiple modeling techniques for constructing the model (908). In some examples, the multiple modeling techniques include ordinary differential equations (ODEs), systems of ODEs, partial differential equations (PDEs), systems of PDEs, Flux Balance Analyses, Monte-carlo simulations, and Boolean networks.

In some implementations, the process 900 further includes compiling the subset of biological data into configuration data of a second format that is specific to the modeling technique and that is different from the first format (910) and generating the model using the modeling technique and the configuration data (912). In some examples, the second format is a structured format. In some examples, the process 900 further includes receiving a third selection of the behavior of the biological system and receiving the subset of data of the biological data based in part on the third selection of the behavior of the biological system. In some examples, generating the model based on the configuration data includes automatically performing technical actions related to generating the model (e.g., and unrelated to a scientific understanding of the biological data).

In some examples, the process 900 further includes executing the model to simulate the behavior of the biological system. In some examples, the process 900 further includes executing the model for one or more additional iterations. In some examples, the process 900 further includes generating results that simulate the behavior of the biological system. In some examples, the process 900 further includes storing the results of the model in the data repository. In some examples, the process 900 further includes generating a graphical output corresponding to the results. In some examples, the process 900 further includes sending the graphical output to a display device. In some examples, the graphical output includes a dynamic representation of the behavior of the biological system. In some examples, the graphical output includes a static representation of the behavior of the biological system.

A computer program (also known as a program, software, software application, script, or code) may be written in any appropriate form of programming language, including compiled or interpreted languages, and it may be deployed in any appropriate form, including as a standalone program or as a module, component, subroutine, or other unit suitable for use in a computing environment. A computer program does not necessarily correspond to a file in a file system. A program may be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program may be deployed to be executed on one computer or on multiple computers that are located at one site or distributed across multiple sites and interconnected by a communication network.

The processes and logic flows described in this specification may be performed by one or more programmable processors executing one or more computer programs to perform functions by operating on input data and generating output. The processes and logic flows may also be performed by, and apparatuses may also be implemented as, special purpose logic circuitry, e.g., an FPGA (field programmable gate array) or an ASIC (application specific integrated circuit).

Processors suitable for the execution of a computer program include, by way of example, both general and special purpose microprocessors, and any one or more processors of any appropriate kind of digital computer. Generally, a processor will receive instructions and data from a read only memory or a random access memory or both. Elements of a computer can include a processor for performing instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. However, a computer need not have such devices. Moreover, a computer may be embedded in another device, e.g., a mobile telephone, a personal digital assistant (PDA), a mobile audio player, a Global Positioning System (GPS) receiver, to name just a few. Computer readable media suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto optical disks; and CD ROM and DVD-ROM disks. The processor and the memory may be supplemented by, or incorporated in, special purpose logic circuitry.

To provide for interaction with a user, implementations may be realized on a computer having a display device, e.g., a CRT (cathode ray tube) or LCD (liquid crystal display) monitor, for displaying information to the user and a keyboard and a pointing device, e.g., a mouse or a trackball, by which the user may provide input to the computer. Other kinds of devices may be used to provide for interaction with a user as well; for example, feedback provided to the user may be any appropriate form of sensory feedback, e.g., visual feedback, auditory feedback, or tactile feedback; and input from the user may be received in any appropriate form, including acoustic, speech, or tactile input.

Implementations may be realized in a computing system that includes a back end component, e.g., as a data server, or that includes a middleware component, e.g., an application server, or that includes a front end component, e.g., a client computer having a graphical user interface or a Web browser through which a user may interact with an implementation, or any appropriate combination of one or more such back end, middleware, or front end components. The components of the system may be interconnected by any appropriate form or medium of digital data communication, e.g., a communication network. Examples of communication networks include a local area network ("LAN") and a wide area network ("WAN"), e.g., the Internet.

The computing system may include clients and servers. A client and server are generally remote from each other and typically interact through a communication network. The relationship of client and server arises by virtue of computer programs running on the respective computers and having a client-server relationship to each other.

Figure 10:
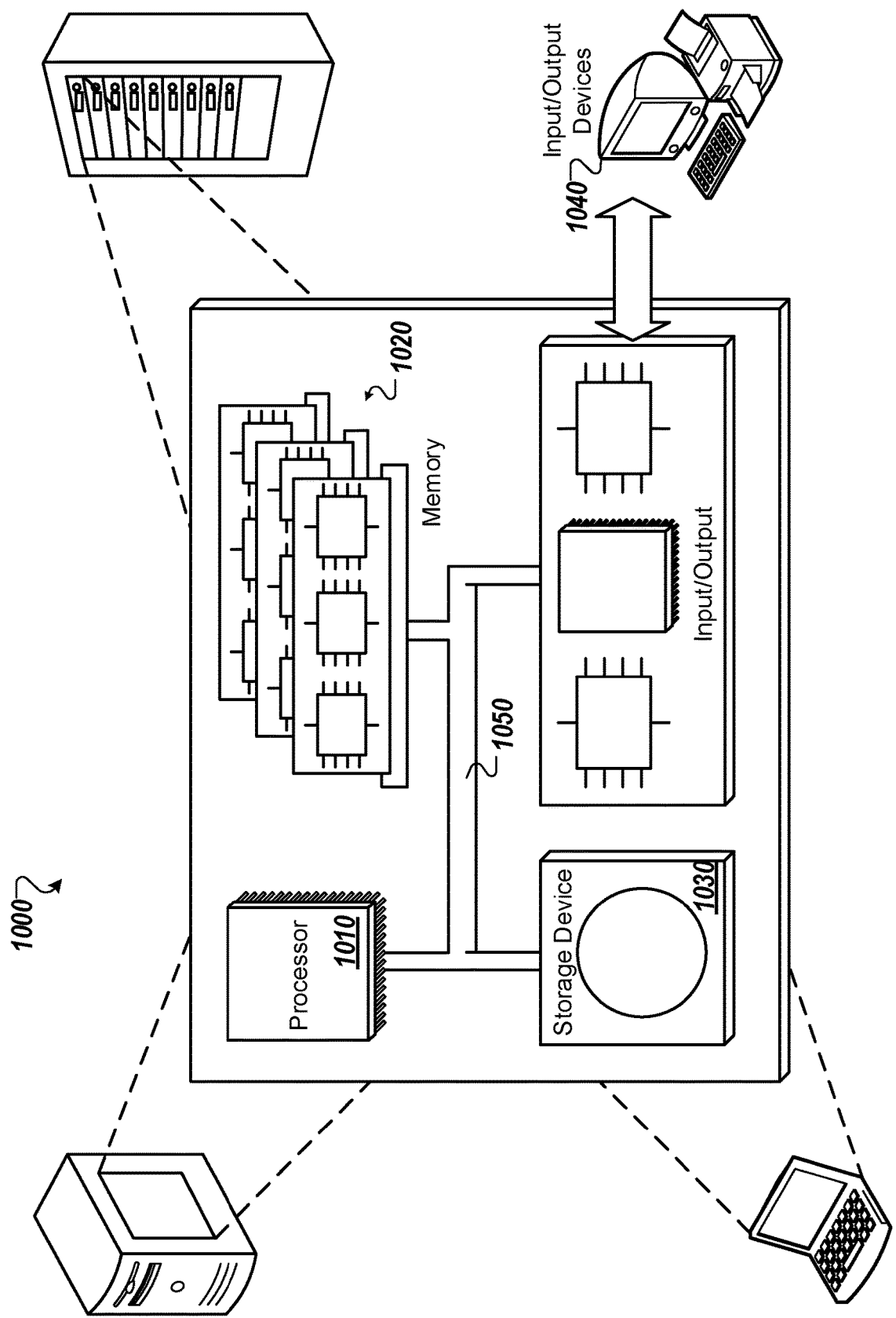
FIG. 10 depicts an example computing system that can execute implementations of the present disclosure.

FIG. 10 depicts an example computing system 1000 that can execute implementations of the present disclosure. The computing system 1000 can be used for the operations described in association with any of the computer-implement methods described previously, according to one implementation. The computing system 1000 includes a processor 1010, a memory 1020, a storage device 1030, and an input/output device 1040. Each of the components 1010, 1020, 1030, and 1040 are interconnected using a system bus 1050. The processor 1010 is capable of processing instructions for execution within the computing system 1000. In one implementation, the processor 1010 is a single-threaded processor. In another implementation, the processor 1010 is a multi-threaded processor. The processor 1010 is capable of processing instructions stored in the memory 1020 or on the storage device 1030 to display graphical information for a user interface on the input/output device 1240.

The memory 1020 stores information within the computing system 1000. In one implementation, the memory 1020 is a computer-readable medium. In one implementation, the memory 1020 is a volatile memory unit. In another implementation, the memory 1020 is a non-volatile memory unit.

The storage device 1030 is capable of providing mass storage for the computing system 1000. In one implementation, the storage device 1030 is a computer-readable medium. In various different implementations, the storage device 1030 may be a floppy disk device, a hard disk device, an optical disk device, or a tape device.

The input/output device 1040 provides input/output operations for the computing system 1000. In one implementation, the input/output device 1040 includes a keyboard and/or pointing device. In another implementation, the input/output device 1040 includes a display unit for displaying graphical user interfaces.

While this specification contains many specifics, these should not be construed as limitations on the scope of the disclosure or of what may be claimed, but rather as descriptions of features specific to particular implementations. Certain features that are described in this specification in the context of separate implementations may also be implemented in combination in a single implementation. Conversely, various features that are described in the context of a single implementation may also be implemented in multiple implementations separately or in any suitable subcombination. Moreover, although features may be described above as acting in certain combinations and even initially claimed as such, one or more features from a claimed combination may in some cases be excised from the combination, and the claimed combination may be directed to a sub-combination or variation of a sub-combination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the implementations described above should not be understood as requiring such separation in all implementations, and it should be understood that the described program components and systems may generally be integrated together in a single software product or packaged into multiple software products.

A number of implementations have been described. Nevertheless, it will be understood that various modifications may be made without departing from the spirit and scope of the disclosure. For example, various forms of the flows shown above may be used, with steps re-ordered, added, or removed. Accordingly, other implementations are within the scope of the following claims.

What is claimed is:

1. A method performed by one or more computers, the method comprising:

maintaining biological data related to a plurality of biological systems in a data repository;

receiving, via one or more user interfaces, a first selection of a biological system of the plurality of biological systems for generating a model that simulates a behavior of the biological system, wherein the model is a computational model;

retrieving a subset of data of the biological data from multiple entries in the data repository, wherein the biological data is associated with the first selection of the biological system, and wherein the data repository specifies reactions of multiple biological objects represented in the multiple entries, and wherein at least one of the multiple biological objects corresponds to at least part of the biological system;

receiving, via the one or more user interfaces, a second selection of a modeling technique of a plurality of modeling techniques for generating the model;

determining that the data repository lacks at least some other biological data for simulating the behavior of the biological system using the model, wherein the at least some other biological data comprises a listing of the reactions that are active for a set of conditions, wherein the set of conditions comprises temperature or nutrients in media;

in response to the determination, performing in silico experiments over a range of conditions in the set of conditions;

predicting the at least some other biological data using the performed in silico experiments, wherein the at least some other biological data predicted comprises uptake of components or growth rates;

compiling the subset of data with the predicted at least some other biological data into configuration data that is specific to the modeling technique;

generating the model using the modeling technique and the configuration data;

simulating the behavior of the biological system by executing the model; and outputting one or more results from executing the model in the data repository.

2. The method of claim 1, wherein the plurality of biological systems comprises a biological system selected from a group consisting of: an organism, a portion of organism, a gene, DNA, RNA, a protein, and a small molecule.

3. The method of claim 1, wherein the behavior is associated with a process selected from a group consisting of: a process comprising biochemical reactions, a molecular complexation process, DNA replication, DNA maintenance, RNA transcription, a process involving a gene regulatory network, intracellular transport, and transmembrane transport.

4. The method of claim 1, further comprising:
receiving a third selection of the behavior of the biological system; and
receiving the subset of data of the biological data based in part on the third selection of the behavior of the biological system.

5. The method of claim 1, wherein the plurality of modeling techniques comprises ordinary differential equations (ODEs), systems of ODEs, partial differential equations (PDEs), systems of PDEs, Flux Balance Analyses, Monte-carlo simulations, and Boolean networks.

6. The method of claim 1, further comprising generating a graphical output corresponding to the results.

7. The method of claim 6, further comprising sending the graphical output to a display device.

8. The method of claim 6, wherein the graphical output comprises a dynamic representation of the behavior of the biological system.

9. The method of claim 6, wherein the graphical output comprises a static representation of the behavior of the biological system.

10. The method of claim 1, further comprising executing the model for one or more additional iterations.

11. The method of claim 1, wherein generating the model comprises, without receiving input from a user, choosing time step sizes, choosing probability distributions, performing parameter fitting, performing spatial discretization, or performing numerical integrator tuning.

12. The method of claim 1, further comprising receiving the biological data in the data repository.

13. The method of claim 1, wherein:
the modeling technique is a first modeling technique, the method further comprising:
after receiving, via the one or more user interfaces, a third selection of a second modeling technique and before receiving, from the user, the second selection of the first modeling technique, prompting the user to select a different modeling technique.

14. The method of claim 1, wherein:
the modeling technique is flux balance analysis,
generating the model comprises:
determining which genes are present or absent in a biological organism of the biological system, and
including only reactions that are enabled by genes that are present, constructing the model comprises, without input from a user:
generating a mathematical representation of a set of parameters for the flux balance analysis of the biological system that can be solved through linear optimization, and
generating an objective function from the biological system, and
executing the model comprises optimizing the objective function by varying values of the parameters of the set of parameters.

15. The method of claim 14, further comprising:
determining active genes among genes that are present based on the performed in silico experiments, wherein the subset of data comprises only the reactions that are enabled by the active genes.

16. The method of claim 1, wherein the data repository identifies at least some of the reactions between the multiple biological objects using one or more cross-indices or one or more cross-references.

17. The method of claim 1, wherein the data repository includes a bipartite graph structure, and wherein the data repository identifies at least some of the reactions between the multiple biological objects using one or more edges in the bipartite graph structure.

18. The method of claim 1, further comprising:
receiving an identification of one or more characteristics of the biological system; and
transforming the one or more characteristics into one or more constraints to be imposed on the model, wherein the transformation is performed based on an architecture of the model,
wherein the execution of the model includes imposing the one or more constraints.

19. A non-transitory computer-readable storage medium coupled to one or more processors and having instructions stored thereon which, when executed by the one or more processors, cause the one or more processors to perform operations comprising:
maintaining biological data related to a plurality of biological systems in a first format in a data repository;
receiving, via one or more user interfaces, a first selection of a biological system of the plurality of biological systems for generating a model that simulates a behavior of the biological system, wherein the model is a computational model;
retrieving a subset of data of the biological data from multiple entries in the data repository, wherein the biological data is associated with the first selection of the biological system, and wherein the data repository specifies reactions of multiple biological objects represented in the multiple entries, and wherein at least one of the multiple biological objects corresponds to at least part of the biological system;
receiving, via the one or more user interfaces, a second selection of a modeling technique of a plurality of modeling techniques for generating the model;
determining that the data repository lacks at least some other biological data for simulating the behavior of the biological system using the model, wherein the at least some other biological data comprises a listing of the reactions that are active for a set of conditions, wherein the set of conditions comprises temperature or nutrients in media;

in response to the determination, performing in silico experiments over a range of conditions in the set of conditions;

predicting the at least some other biological data using the performed in silico experiments, wherein the at least some other biological data predicted comprises uptake of components or growth rates;

compiling the subset of data with the predicted at least some other biological data into configuration data that is specific to the modeling technique;

generating the model using the modeling technique and the configuration data;

simulating the behavior of the biological system by executing the model; and outputting one or more results from executing the model in the data repository.

20. A system, comprising:

one or more processors; and a computer-readable storage device coupled to the one or more processors and having instructions stored thereon which, when executed by the one or more processors, cause the one or more processors to perform operations comprising:

maintaining biological data related to a plurality of biological systems in a data repository;

receiving, via one or more user interfaces, a first selection of a biological system of the plurality of biological systems for generating a model that simulates a behavior of the biological system, wherein the model is a computational model,;

retrieving a subset of data of the biological data from multiple entries in the data repository, wherein the biological data is associated with the first selection of the biological system, and wherein the data repository specifies reactions of multiple biological objects represented in the multiple entries, and wherein at least one of the multiple biological objects corresponds to at least part of the biological system;

receiving, via the one or more user interfaces, a second selection of a modeling technique of a plurality of modeling techniques for generating the model;

determining that the data repository lacks at least some other biological data for simulating the behavior of the biological system using the model, wherein the at least some other biological data comprises a listing of the reactions that are active for a set of conditions, wherein the set of conditions comprises temperature or nutrients in media;

in response to the determination, performing in silico experiments over a range of conditions in the set of conditions;

predicting the at least some other biological data using the performed in silico experiments, wherein the at least some other biological data predicted comprises uptake of components or growth rates;

compiling the subset of data with the predicted at least some other biological data into configuration data that is specific to the modeling;

generating the model using the modeling technique and the configuration data;

simulating the behavior of the biological system by executing the model; and outputting one or more results from executing the model in the data repository.

* * * * *